US006849642B2

(12) United States Patent
Gerlach et al.

(10) Patent No.: US 6,849,642 B2
(45) Date of Patent: Feb. 1, 2005

(54) BICYCLIC IMIDAZO-3-YL-AMINE DERIVATIVES SUBSTITUTED ON THE 6-MEMBERED RING

(75) Inventors: Matthias Gerlach, Brachttal (DE); Corinna Maul, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/117,334

(22) Filed: Apr. 8, 2002

(65) Prior Publication Data

US 2002/0183327 A1 Dec. 5, 2002

Related U.S. Application Data

(63) Continuation of application No. PCT/EP00/09095, filed on Sep. 18, 2000.

(30) Foreign Application Priority Data

Oct. 8, 1999 (DE) .......................................... 199 48 434
Oct. 8, 1999 (DE) .......................................... 199 48 437

(51) Int. Cl.$^7$ ..................... A61K 31/437; C07D 471/00
(52) U.S. Cl. ..................... 514/300; 514/292; 546/84; 546/121; 471/4
(58) Field of Search ................................. 514/292, 300; 546/84, 121

(56) References Cited

U.S. PATENT DOCUMENTS 4,450,164 A * 5/1984 Bristol et al. ................ 514/303

FOREIGN PATENT DOCUMENTS

| EP | 0068378 | 1/1983 |
|----|---------|--------|
| EP | 0266890 | 5/1988 |
| EP | 0518033 | 12/1992 |
| EP | 0822194 | 2/1998 |
| GB | 1135893 | 12/1968 |

OTHER PUBLICATIONS

CAS printout for Bienayme et al. Chem. Abs. 129:302566.*
CAS printout for Klopman et al. Chem. Abs. 113:126044.*
Rajender S. Varma, et al., "Microwave–accelerated three component condensation reaction on clay: solvent–free synthesis of imidazo[1,3–a] annulated pyridines, pyrazines and pyrimidines" Tetrahedron Letters, vol. 40, 1999, pp. 7665–7669.
Luigi Amerante, et al., "Derivatives of Imidazole. III. Synthesis and Pharmacological Activities of Nitriles, Amides, and Carboxylic Acid Derivatives of Imidazo[1,2–a] pyridine" J. Chem. Sci., vol. 12, Jan. 1969.

MG Rimoli, et al., "Research on heterocycle compounds. XXXVII. Synthesis and antiinflammatory activity of methyl–substituted imidazo[1,2–a]pyrazine derivatives" Eur. J. Med. Chem, vol. 32, 1997, pp. 195–203.
Sonia Laneri, et al., Research on heterocylic compounds – Part XXXIX. 2–Methylimidazo[1,2–a] pyrimidine–3–carboxylic derivatives: Synthesis and antiinflammatory activity Eur. J. Med. Chem, vol. 33, 1998, pp. 163–170.
A. Sacchi, et al., "Research on heterocyclic compounds. Part XXXVI. Imidazo[1,2–a]pyrimidine–2–acetic derivatives: synthesis and antiinflammatory activity" Eur. J. Med. Chem, vol. 32, 1997, pp. 677–682.
John P. Devlin, "High Throughput Screening" 1997.
James Kaminski, et al., "Antiulcer Agents. 2. Gastric Antisecretory, Cytoprotective, and Metabolic Properties of Substituted Imidazo[1,2–a]pyridines and Analogues" J. Med. Chem. 1987, vol. 30, pp. 2031–2046.
Yveline Rival, et al., "Synthesis and Antibacterial Activity of Some Imidazo[1,2–a]pyrimidine Derivatives" Chem. Pharm. Bulletin, vol. 40, 1992, pp. 1170–1176.
Alan Gueiffier, et al., "Synthesis of Imidazo[1,2–a]pyridines as Antiviral Agents" J. Med. Chem., vol. 77, 1998.
Christopher Blackburn, "A Three–Component Solid–Phase Synthesis of 3–Aminoimidazo[1,2–a]azines" Tetrahedron Letters, vol. 39, 1998, pp. 5469–5472.
Christopher Blackburn, et al., "Parallel Synthesis of 3–Aminoimidazo[1,2–a]pyridines and pyrazines by a New Three–Component Condensation" Tetrahedron Letters, vol. 39, 1998, pp. 3635–3638.
Gordon Barlin, et al., Imidazo[1,2–b]pyridazines: Synthesis and Interaction with Central and Peripheral–Type (Mitochondrial) Benzodiazepine Receptors J. Heterocyclic Chem., vol. 35, 1998.
Michael H. Fisher, et al., "Imidazo[1,2–a]pyridine Anthelmintic and Antifungal Agents" J. of Med. Chem. vol. 15, No. 9, 1972.
Katrin Groebke, et al., "Synthesis of Imidazo[1,2–a] annulated Pyridines, Pyrazines, and Pyrimidines by a Novel Three–Component Condensation" Synlett, Jun. 1998.
Hughes Bienayme, et al., "Eine neue heterocyclishe Mehrkomponenten–reaktion fure die kombinatorishe Synthese von anellierten 3–Aminoimidazlen" Angew. Chem. 1998.

* cited by examiner

*Primary Examiner*—Richard L. Raymond
(74) *Attorney, Agent, or Firm*—Crowell & Moring LLP

(57) ABSTRACT

Bicyclic imidazo-3-yl-amine derivatives substituted on the 6-membered ring, and pharmaceutical compositions containing these compounds, useful, inter alia, as analgesics.

13 Claims, No Drawings

BICYCLIC IMIDAZO-3-YL-AMINE DERIVATIVES SUBSTITUTED ON THE 6-MEMBERED RING

CROSS REFERENCE TO RELATED APPLICATIONS

The present application is a continuation of international patent application no. PCT/EP00/09095, filed Sep. 18, 2000, designating the United States of America, the entire disclosure of which is incorporated herein by reference. Priority is claimed based on Federal Republic of Germany patent application nos. 199 48 437.6 and 199 48 437.6, both filed on Oct. 8, 1999.

BACKGROUND OF THE INVENTION

The present invention relates to bicyclic imidazo-3-yl amine derivatives substituted on the 6-membered ring, processes for their preparation, methods of treatment using these compounds, and pharmaceutical compositions containing these compounds.

Individual compounds from the class of imidazo-3-yl amines are known to have interesting pharmacological properties. For example, specific imidazo [1,2-a]pyridines are described as antihypertensive substances (GB-B-135,893), as anthelmintics and antimycotics (J. Med. Chem. 1972, 15, 982–985), and as anti-secretory active substances for treating inflammatory conditions (EP-A-0 068 378). EP-A-0 266 890 and J. Med. Chem. 1987, 30, 2031–2046 also describe the action of individual imidazopyridines against inflammatory conditions, particularly gastric inflammatory conditions. Further pharmacological effects described for individual members of the class of imidazo-3-yl amines include antibacterial properties (Chem. Pharm. Bull. 1992, 40, 1170), antiviral properties (J. Med. Chem. 1998, 41, 5108–5112) as well as their action as bezodiazepine receptor antagonists (J. Heterocyclic Chem. 1998, 35, 1205–1217).

In view of these interesting pharmacological properties, various members of the class of substituted imidazo-3-yl amines have been synthesized in the past. In particular, attempts have been made to increase the number of available substituted imidazo-3-yl amines by combinatorial synthesis processes. For example, C. Blackburn et al. in Tetrahedron Lett. 1998, 39, 5469–5472 describe a three-component solid phase synthesis for preparing imidazo-3-yl amines, while Tetrahedron Lett. 1998, 39, 3635–3638 describes a three-component condensation for the parallel synthesis of imidazo-3-yl amines. The synthesis published by K. Groebke et al. in Synlett. 1998, 661–663 is similar to the last-mentioned reaction. H. Bienayme and K. Bouzid in Angew. Chem. 1998, 110 (16), 2349–2352 also describe a multi-component reaction for the combinatorial synthesis of imidazo-3-yl amines, by means of which imidazo-5-amines have also been prepared.

However, the range of possible substituents on the amino nitrogen atom and in the 2-position of the imidazole ring was limited.

Accordingly, the present invention provides further bicyclic imidazo-3-yl amines in which at least one substituent on the amino group and on the atoms of the 6-membered ring not belonging to the imidazole ring as well as the substituent in the 2-position of the imidazole ring are different from hydrogen. In another embodiment, the present invention provides medicaments and pharmaceutical compositions containing these compounds, and methods of treating patients in need thereof with these compounds.

The present invention provides bicyclic imidazo-3-yl amines of general formula I,

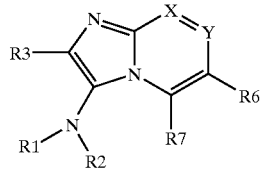

I wherein

X denotes $CR^4$ or N and Y denotes $CR^6$ or N, with the proviso that X and Y do not simultaneously denote N, $R^1$ denotes $(CH_2)_n CN$ where n=4, 5 or 6, optionally substituted phenyl, $C_4$–$C_8$-cycloalkyl, $CH_2CH_2R$ (R=4-morpholino), 1,1,3,3-tetramethylbutyl or $CH_2R^a$ wherein $R^a$ denotes hydrogen, OH, $C_1$–$C_8$-alkyl (branched or unbranched), optionally substituted phenyl, CO(OR') (where R'=unbranched $C_1$–$C_4$-alkyl or branched $C_1$–$C_5$-alkyl), $PO(OR')_2$ (where R'=unbranched $C_1$–$C_5$-alkyl or branched $C_1$–$C_6$-alkyl) or $Si(R^x R^y R^z)$ (where $R^x$, $R^y$ and $R^z$ in each case independently of one another denote $C_1$–$C_4$-alkyl (branched or unbranched), $C_4$–$C_8$-alkyl or phenyl, $R^2$ denotes hydrogen, $COR^b$, wherein $R^b$ denotes $C_1$–$C_4$-alkyl (branched or unbranched) or $C_3$–$C_8$-cycloalkyl, $CH_2CH_2CO(OR^c)$, wherein $R^c$ denotes $C_1$–$C_4$-alkyl (branched or unbranched), adamantyl, optionally substituted phenyl, optionally substituted 1-naphthyl or 2-naphthyl, or in each case optionally substituted 2-pyridyl, 3-pyridyl, 4-pyridyl, thiazolyl or furoyl, $CH_2$phenyl, $CH_2CH_2R^d$, wherein $R^d$ denotes optionally substituted phenyl, or $CONHR^e$, wherein $R^e$ denotes $C_1$–$C_8$-alkyl (branched or unbranched), $C_3$–$C_8$-cycloalkyl or optionally substituted phenyl, $R^3$ denotes $C_1$–$C_8$-alkyl (branched or unbranched), $C_3$–$C_8$-cycloalkyl, optionally substituted phenyl, optionally substituted naphthyl, optionally substituted pyrrole, optionally substituted pyridyl, optionally substituted furan, optionally substituted thiophene, optionally substituted anthracene, optionally substituted phenanthrene or optionally substituted quinoline, $R^4$, $R^5$, $R^6$ and $R^7$ in each case independently of one another denote hydrogen, $C_1$–$C_4$-alkyl (branched or unbranched), $NO_2$, $NH_2$, OH, $CF_3$, Cl, F, Br, CN, COOR, wherein R denotes hydrogen, $C_1$–$C_4$-alkyl (branched or unbranched), OR", wherein R" denotes optionally substituted phenyl, optionally substituted benzyl, or $C_1$–$C_4$-alkyl (branched or unbranched), or $R^4$ and $R^5$, $R^5$ and $R^6$ or $R^6$ and $R^7$ denote a 4-membered carbon bridge optionally containing at least one double bond in which individual C atoms may be optionally replaced by heteroatoms such as N, O or S, and all the remaining radicals $R^4$, $R^5$, $R^6$ and $R^7$ that do not form the bridge denote hydrogen, with the proviso that at least one of the radicals $R^4$, $R^5$, $R^6$ or $R^7$ present in the molecule is not hydrogen, and if $R^1$ denotes methyl, ethyl, propyl, n-butyl, iso-butyl, CO(O-methyl) or benzyl, $R^3$ does not denote methyl, and if one of the radicals $R^4$, $R^5$, $R^6$ and $R^7$ denotes O-benzyl or $R^4$ denotes $OC_1$–$C_4$-alkyl (branched or unbranched), then $R^1$ does not denote $CH_2R^a$ (wherein $R^a$ denotes hydrogen or $C_1$–$C_5$-alkyl (branched or unbranched), in the form of the bases or pharmaceutically acceptable salts.

Preferred compounds according to the invention are those in which $R^4$ denotes hydrogen, $R^1$ is selected from the group consisting of $(CH_2)_n CN$ where n=4, 5 or 6, cyclohexyl, $CH_2CO(O-methyl)$, 2,6-dimethylphenyl, 1,1,3,3-tetramethylbutyl and n-butyl, and $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3- dichlorophenyl, 2,4-dichlorophenyl, 2-methoxyphenyl, 2,3-dimethoxyphenyl, 3-bromophenyl, 4-bromo-2-fluorophenyl, 5-bromo-2-fluoro-phenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)-phenyl.

The radicals $R^4$, $R^5$, $R^6$ and $R^7$ are, according to the invention, preferably selected either from the group consisting of hydrogen, $NO_2$, $NH_2$, OH, $CF_3$, Cl, F, Br, CN, methyl and OR" where R"=benzyl, wherein at least one of the radicals $R^4$, $R^5$, $R^6$ and $R^7$ must be different from hydrogen, or $R^6$ and $R^7$ together form a bridge —CH=CH—CH=CH— and the radicals $R^4$ and $R^5$, insofar as they are present, denote hydrogen.

Particularly preferred according to the invention are bicyclic imidazo-3-yl amine derivatives substituted on the 6-membered ring selected from the group consisting of 7-chloro-2-furan-2-yl-(6-isocyanohexyl)-imidazo[1,2-a]pyrimidine-3,5-diamine,
(5,7-dimethyl-2-pyridin-2-yl-imidazo[1,2-a]-pyrimidin-3-yl)-(6-isocyanohexyl)amine,
7-chloro-(1,1,3,3-tetramethylbutyl)-2-thiopen-2-yl-imidazo[1,2-a]pyrimidine-3,5-diamine,
[6-bromo-2-(2-methoxyphenyl)-imidazo[1,2-a]pyridin-3-yl]-1,1,3,3-tetramethyl]butyl)-amine,
N-[4-(8-benzyloxy-3-cyclohexylaminoimidazo[1,2-a]pyridin-2-yl)-phenyl]-acetamide,
3-(8-benzyloxy-3-butylaminoimidazo[1,2-a]pyridin-2-yl)-phenol,
[8-benzyloxy-2-(3,5-dimethoxyphenyl)-imidazo[1,2-a]pyridin-3-ylamino]-acetic acid methyl ester,
[8-benzyloxy-2-(3,5-dimethoxyphenyl)-imidazo[1,2-a]pyridin-3-yl]-cyclohexylamine,
cyclohexyl-[6,8-dibromo-2-(2-methoxyphenyl)-5-methyl-imidazo[1,2-a]pyridin-3-yl]-amine,
3-[3-(2,6-dimethylphenylamino)-6-nitroimidazo[1,2-a]pyridin-2-yl]-phenol,
[6-bromo-2-(2-methoxyphenyl)-imidazo[1,2-a]pyridin-3-yl]-(1,1,3,3-tetramethylbutyl)-amine,
[6,8-dibromo-2-(2,3-dimethoxyphenyl)-5-methylimidazo[1,2-a]pyridin-3-yl]-(1,1,3,3-tetramethylbutyl)-amine,
cyclohexyl-(2-phenylimidazo[1,2-a]quinolin-1-yl)-amine,
[6-(2-cyclohexyl)-5-methylimidazo[1,2-a]pyridin-3-ylamino)-hexyl]-methylidyne ammonium,
(2,6-dimethylimidazo[1,2-a]pyridin-3-yl)-(1,1,3,3-tetramethylbutyl)-amine,
cyclohexyl-(2,7-dimethylimidazo[1,2-a]pyridin-3-yl)-amine,
cyclohexyl-(2,5,7-trimethylimidazo[1,2-a]pyridin-3-yl)-amine,
[2-(3,4-dimethoxyphenyl)-6-methylimidazo[1,2-a]pyridin-3-yl]-(6-isocyanohexyl)-amine,
(2,7-dimethylimidazo[1,2-a]pyridin-3-yl)-(1,1,3,3-tetramethylbutyl)-amine,
(2,8-dimethyl-imidazo[1,2-a]pyridin-3-yl)-(1,1,3,3-tetramethylbutyl)-amine,
(1,1,3,3-tetramethylbutyl)-(2,5,7-trimethylimidazo[1,2-a]pyridin-3-yl)-amine,
[2-(3,4-dimethoxyphenyl)-7-methylimidazo[1,2-a]pyridin-3-yl]-(6-isocyanohexyl)-amine,
(6-isocyanohexyl)-[2-(2-methoxyphenyl)-6-methyl-imidazo[1,2-a]pyridin-3-yl]-amine,
cyclohexyl-(2-furan-2-yl-6-trifluoromethylimidazo[1,2-a]pyridin-3-yl)-amine,
(8-benzyloxy-2-cyclohexylimidazo[1,2-a]pyridin-3-yl)-cyclohexylamine,
(8-benzyloxy-2-methylimidazo[1,2-a]pyridin-3-yl)-cyclohexylamine,
(8-benzyloxy-2-methylimidazo[1,2-a]pyridin-3-yl)-(1,1,3,3-tetramethylbutyl)-amine,
(8-benzyloxy-2-cyclohexylimidazo[1,2-a]pyridin-3-ylamino)-acetic acid methyl ester,
(8-benzyloxy-2-methylimidazo[1,2-a]pyridin-3-ylamino)-acetic acid methyl ester,
butyl-(2-cyclohexyl-5-propylimidazo[1,2-a]pyridin-3-yl)-amine
N-cylcohexyl-N-(6,8-dichloro-2-furan-2-yl-imidazo[1,2-a]pyridin-3-yl)-acetamide,
N-cylcohexyl-N-(2-furan-2-yl-6-trifluoromethylimidazo[1,2-a]pyridin-3-yl)-acetamide,
N-(8-benzyloxy-2-cyclohexylimidazo[1,2-a]pyridin-3-yl)-N-cyclohexylacetamide,
(5-methyl-2-phenanthren-9-yl-imidazo[1,2-a]pyridin-3-yl)-(1,1,3,3-tetramethylbutyl)-amine,
(2-anthracen-9-yl-7-methylimidazo[1,2-a]pyridin-3-yl)-(1,1,3,3-tetramethylbutyl)-amine, and
cyclohexyl-[7-methyl-2-(1-methyl-1H-pyrrol-2-yl)-imidazo[1,2-a]pyrimidin-3-yl]-amine.

Insofar as the bicyclic imidazo-3-yl amine derivatives according to the invention substituted on the 6-membered ring contain optically active carbon atoms, any enantiomer of these compounds, and mixtures thereof in any ratio, are also the subject of the present invention.

The invention also provides medicaments and pharmaceutical compositions containing as an active substance at least one bicyclic imidazo-3-yl amine of general formula I in which $R^1$ to $R^7$, X and Y have the aforementioned meanings, in the form of the base, or in the form of a pharmaceutically acceptable salt, preferably of hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid or in particular of hydrochloric acid.

Surprisingly, the compounds according to the invention are not only potential active substances for the conditions mentioned in the prior art, but also exhibit an analgesic effect.

The medicaments and pharmaceutical compositions according to the invention particularly preferably contain as active substance at least one bicyclic imidazo-3-yl amine selected from the group consisting of 7-chloro-2-furan-2-yl-(6-isocyanohexyl)-imidazo[1,2-a]pyrimidine-3,5-diamine,
(5,7-dimethyl-2-pyridin-2-yl-imidazo[1,2-a]-pyrimidin-3-yl)-(6-isocyanohexyl)amine,
7-chloro-(1,1,3,3-tetramethylbutyl)-2-thiopen-2-yl-imidazo[1,2-a]pyrimidine-3,5-diamine,
[6-bromo-2-(2-methoxyphenyl)-imidazo[1,2-a]pyridin-3-yl]-1,1,3,3-tetramethyyl]butyl)-amine,
N-[4-(8-benzyloxy-3-cyclohexylaminoimidazo[1,2-a]pyridin-2-yl)-phenyl]-acetamide,
3-(8-benzyloxy-3-butylaminoimidazo[1,2-a]pyridin-2-yl)-phenol,
[8-benzyloxy-2-(3,5-dimethoxyphenyl)-imidazo[1,2-a]pyridin-3-ylamino]-acetic acid methyl ester,
[8-benzyloxy-2-(3,5-dimethoxyphenyl)-imidazo[1,2-a]pyridin-3-yl]-cyclohexylamine,
cyclohexyl-[6,8-dibromo-2-(2-methoxyphenyl)-5-methyl-imidazo[1,2-a]pyridin-3-yl]-amine,
3-[3-(2,6-dimethylphenylamino)-6-nitroimidazo[1,2-a]pyridin-2-yl-]-phenol,

[6-bromo-2-(2-methoxyphenyl)-imidazo[1,2-a]pyridin-3-yl]-(1,1,3,3-tetramethylbutyl)-amine,
[6,8-dibromo-2-(2,3-dimethoxyphenyl)-5-methylimidazo[1,2-a]pyridin-3-yl]-(1,1,3,3-tetramethylbutyl)-amine,
cyclohexyl-(2-phenylimidazo[1,2-a]quinolin-1-yl)-amine,
[6-(2-cyclohexyl]-5-methylimidazo[1,2-a]pyridin-3-ylamino)-hexyl]-methylidyne ammonium,
(2,6-dimethylimidazo[1,2-a]pyridin-3-yl)-(1,1,3,3-tetramethylbutyl)-amine,
cyclohexyl-(2,7-dimethylimidazo[1,2-a]pyridin-3-yl)-amine,
cyclohexyl-(2,5,7-trimethylimidazo[1,2-a]pyridin-3-yl)-amine,
[2-(3,4-dimethoxyphenyl)-6-methylimidazo[1,2-a]pyridin-3-yl]-(6-isocyanohexyl)-amine,
(2,7-dimethylimidazo[1,2-a]pyridin-3-yl)-(1,1,3,3-tetramethylbutyl)-amine,
(2,8-dimethyl-imidazo[1,2-a]pyridin-3-yl)-(1,1,3,3-tetramethylbutyl)-amine,
(1,1,3,3-tetramethylbutyl)-(2,5,7-trimethylimidazo[1,2-a]pyridin-3-yl)-amine,
[2-(3,4-dimethoxyphenyl)-7-methylimidazo[1,2-a]pyridin-3-yl]-(6-isocyanohexyl)-amine,
(6-isocyanohexyl)-[2-(2-methoxyphenyl)-6-methyl-imidazo[1,2-a]pyridin-3-yl]-amine,
cyclohexyl-(2-furan-2-yl-6-trifluoromethylimidazo[1,2-a]pyridin-3-yl)-amine,
(8-benzyloxy-2-cyclohexylimidazo[1,2-a]pyridin-2-yl)-cyclohexyl-amine,
(8-benzyloxy-2-methyl-imidazo[1,2-a]pyridin-2-yl)-cyclohexyl-amine,
(8-benzyloxy-2-methylimidazo[1,2-a]pyridin-3-yl)-(1,1,3,3-tetramethylbutyl)-amine,
(8-benzyloxy-2-cyclohexylimidazo[1,2-a]pyridin-3-ylamino)-acetic acid methyl ester,
(8-benzyloxy-2-methylimidazo[1,2-a]pyridin-3-ylamino)-acetic acid methyl ester,
butyl-(2-cyclohexyl-5-propylimidazo[1,2-a]pyridin-3-yl)-amine,
N-cylcohexyl-N-(6,8-dichloro-2-furan-2-yl-imidazo[1,2-a]pyridin-3-yl)-acetamide,
N-cylcohexyl-N-(2-furan-2-yl-6-trifluoromethylimidazo[1,2-a]pyridin-3-yl)-acetamide,
N-(8-benzyloxy-2-cyclohexylimidazo[1,2-a]pyridin-3-yl)-N-cyclohexyl-acetamide,
(5-methyl-2-phenanthren-9-yl-imidazo[1,2-a]pyridin-3-yl)-(1,1,3,3-tetramethylbutyl)-amine,
(2-anthracen-9-yl-7-methylimidazo[1,2-a]pyrimidin-3-yl)-(1,1,3,3-tetramethylbutyl)-amine,
cyclohexyl-[7-methyl-2-(1-methyl-1H-pyrrol-2-yl)-imidazo[1,2-a]pyrimidin-3-yl]-amine, and the pharmaceutically acceptable salts of these compounds.

The compounds according to the invention prove to be effective as ligands for the pain-relevant α2-subtype of the human α-adrenergic receptor. It is therefore particularly preferred to use the bicyclic imidazo-5-yl amine derivatives according to the invention in conjunction with one or more auxiliary substances in order to produce a medicinal drug to control pain.

In order to produce corresponding medicaments or pharmaceutical compositions, in addition to at least one active substance according to the invention auxiliary substances such as carrier materials, fillers, solvents, diluents, colouring agents and/or binders are also used. The choice of auxiliary substances as well as the amounts thereof to be used depends on whether the medicinal drug is to be administered orally, intravenously, intraperitoneally, intradermally, intramuscularly, intranasally, buccally or topically.

Preparations in the form of tablets, coated tablets, capsules, granules, drops, juices and syrups are suitable for oral application, while solutions, suspensions, readily reconstitutable dry preparations as well as sprays are suitable for parenteral, topical and inhalative administration. Active substances according to the invention in depot form, in dissolved form or in a plaster, optionally with the addition of skin penetration promoting agents, are suitable percutaneous application preparations. Forms of preparation that may be employed orally or percutaneously can provide for the delayed release of the active substances according to the invention.

The amount of active substances to be administered to the patient varies depending on the patient's weight, type of application, medical indication, and the severity of the condition.

The compounds according to the invention are synthesized by reacting amidines of general formula II, in particular 2-aminopyridine- and 2-aminopyrimidine derivatives (commercially available from companies such as Acros, Avocado, Aldrich, Fluka, Lancaster, Maybridge, Merck, Sigma or TCI-Jp), with a variety of ketones, or preferably aldehydes III and isonitriles IV, in the presence of 20% perchloric acid according to a three-component reaction. $R^1$ to $R^7$, X and Y have the meanings specified above for the compounds of formula I.

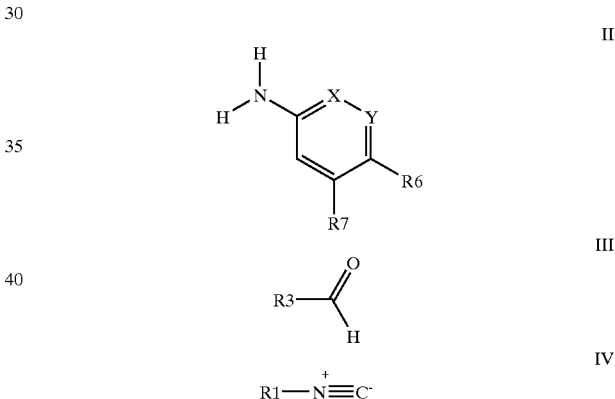

In order for the reaction to proceed in a trouble-free manner, the starting compounds are added one after the other in the sequence amidine II, ketone or aldehyde III, and isonitrile IV. The reactions are preferably carried out in dichloromethane at a temperature of preferably 0° C. to 40° C., in particular at a temperature of 10° C. to 20° C.

In order to prepare the compounds according to the invention in which $R^{2*}$ does not denote hydrogen, the compounds Ia formed in the previously described reaction, which preferably have first of all been dissolved in THF, are reacted, depending on the desired end product, with a compound $R^2$Hal wherein Hal denotes bromine, iodine, or particularly chlorine, for example an optionally substituted alkyl, aryl, or acid chloride, or an optionally substituted isocyanate $R^e$NCO in the presence of a morpholine resin (e.g., polystyrene-morpholine from Argonaut) in dichloromethane within 0.25 to 24 hours at temperatures between 10° C. and 40° C. according to the following reaction scheme:

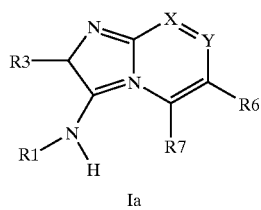

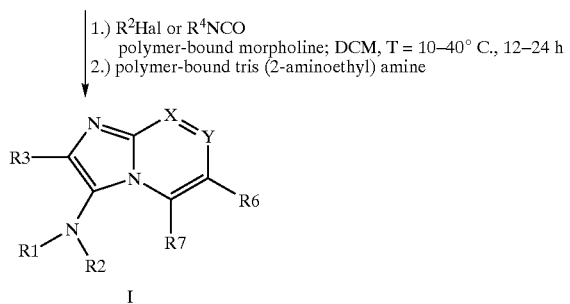

The excess reagents are then removed from the reaction mixture by filtration through a layer with polymer-bound tris(2-aminoethyl)amine (manufacturer: Novabiochem) or 3-(3-mercaptophenyl)propanamidomethylpolystyrene, and the filtrate is then concentrated, preferably in a vacuum centrifuge. The whole process can be carried out without further intervention in an automated synthesis unit.

The compounds of the formula I can be converted in a known manner into their salts with physiologically compatible acids, preferably with hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid.

Hydrochloric acid is particularly preferred. The salt formation is preferably carried out in a solvent, in particular diethyl ether, diisopropyl ether, alkyl esters of acetic acid, acetone or 2-butanone, or a mixture of these solvents. In order to produce the hydrochlorides, trimethyl silane in aqueous solution may also be used.

EXAMPLES

The following examples are intended to illustrate the invention without, however, limiting the scope thereof.

The compounds according to the invention were synthesized in an automated unit from Zymark according to the following general synthesis procedure:

A small threaded glass round-bottomed test tube (diameter 16 mm, length 125 mm) was provided manually with a stirrer and sealed on a capper station with a screw cap provided with a septum. The test tube was placed by robot 1 in the reactor block thermostatically controlled at 15° C. Robot 2 pipetted in the following reagents one after the other:

1.) 1 ml of a 0.1 M amidine solution+20% HClO in dichloromethane
2.) 0.5 ml of a 0.3 M aldehyde solution in dichloromethane
3.) 0.575 ml of a 0.2 M isonitrile solution in dichloromethane.

The reaction mixture was stirred for 660 minutes at 15° C. in one of the stirring blocks. The reaction solution was then filtered oft at the filtration station. The test tube was rinsed twice with in each case 1 ml of dichloromethane and 200 µl of water.

The rack together with the test tubes was then placed manually on the working-up unit. 3 ml of a 10% NaCl solution and 1.5 ml of dichloromethane were then added to the reaction mixture on a vortexer. The reaction mixture was then thoroughly mixed for 10 minutes in the spin reactor, a clear phase boundary forming on slow reduction of the rotational speed. This phase boundary was optically detected and the organic phase was pipetted off. In the next step, a further 1.5 ml of dichloromethane was added to the reaction mixture. The solution was shaken, centrifuged, and the organic phase was pipetted off. The combined organic phases were dried over 2.4 g of $MgSO_4$ (granulated). The solvent was removed in a vacuum centrifuge.

The chemicals and solvents employed were commercially obtained. Each substance was analyzed by ESI-MS and/or NMR.

Example 1

7-chloro-2-furan-2-yl-(6-isocyanohexyl)-imidazo[1,2-a]pyrimidine-3,5-diamine (1)

Compound (1) was prepared according to the general synthesis instructions from 1.0 ml of 2,6-diamino-4-chloropyrimidine solution (0.1 M, DCM), 0.575 ml of 1,6-diisocyanhexane solution (0.2 M, DCM), 0.500 ml of furfural solution (0.3 M, DCM), and 10 µl of perchloric acid (w=20%).

Calculated mass 360.85; found mass 359.2 (ESI-MS)

Example 2

(5,7-dimethyl-2-pyridin-2-yl-imidazo[1,2-a]-pyrimidin-3-yl)-(6-isocyanohexyl)amine (2)

Compound (2) was prepared according to the general synthesis instructions from 1.0 ml of 2-amino-4,6-dimethylpyrimidine solution (0.1 M, DCM), 0.575 ml of 1,6-diisocyanhexane solution (0.2 M, DCM), 0.500 ml of pyridine-2-carbaldehyde solution (0.3 M, DCM), and 10 µl of perchloric acid (w=20%).

Calculated mass 360.85; found mass 359.2 (ESI-MS)

Example 3

(2-cyclohexyl]-5-methylimidazo[1,2-a]pyridin-3-yl)-(1,1,3,3-tetramethylbutyl)-amine (3)

Compound (3) was prepared according to the general synthesis instructions from 1.0 ml of 2-amino-6-methylpyridine solution (0.1 M, DCM), 0.575 ml of 1,1,3,3-tetramethylbutyl isocyanide solution (0.2 M, DCM), 0.500 ml of cyclohexylcarbaldehyde solution (0.3 M, DCM), and 10 µl of perchloric acid (w=20%).

Calculated mass 341.54; found mass 342.4 (ESI-MS)

Example 4

7-chloro-(1,1,3,3-tetramethylbutyl)-2-thiopen-2-yl-imidazo[1,2-a]pyrimidine-3,5-diamine (4)

Compound (4) was prepared according to the general synthesis instructions from 1.0 ml of 2,6-diamino-4-chloropyrimidine solution (0.1 M, DCM), 0.575 ml of 1,1,3,3-tetramethylbutyl isocyanide solution (0.2 M, DCM), 0.500 ml of thiophene-2-carbaldehyde solution (0.3 M, DCM), and 10 µl of perchloric acid (w=20%).

Calculated mass 377.94; found mass 378.3 (ESI-MS)

Example 5

(6-bromo-2-(2-methoxyphenyl)-imidazo[1,2-a]pyridin-3-yl]-1,1,3,3-tetramethyyl]butyl)-amine (5)

Compound (5) was prepared according to the general synthesis instructions from 1.0 ml of 2-amino-5- bromopyridine solution (0.1 M, DCM), 0.575 ml of 1,1,3,3-tetramethylbutyl isocyanide solution (0.2 M, DCM), 0.500 ml of 2-methoxybenzaldehyde solution (0.3 M, DCM), and 10 µl of perchloric acid (w=20%).

Calculated mass 430.39; found mass M+H$_2$O=447.3 (ESI-MS)

Example 6

[6,8-dibromo-2-(2,3-dimethoxyphenyl)-5-methylimidazo[1,2-a]pyridin-3-yl]-(1,1,3,3-tetramethylbutyl)-amine (6)

Compound (6) was prepared according to the general synthesis instructions from 1.0 ml of 2-amino-3,5-dibromo-6-methylpyridine solution (0.1 M, DCM), 0.575 ml of 1,1,3,3-tetramethylbutyl isocyanide solution (0.2 M, DCM), 0.500 ml of 2,3-dimethoxybenzaldehyde solution (0.3 M, DCM), and 10 µl of perchloric acid (w=20%).

Calculated mass 553.34; found mass M+H$_2$O=572.1 (ESI-MS)

Example 7

N-[4-(8-benzyloxy-3-cyclohexylaminoimidazo[1,2-a]pyridin-2-yl)-phenyl]-acetamide (7)

Compound (7) was prepared according to the general synthesis instructions from 1.0 ml of 2-amino-3-benzyloxypyridine solution (0.1 M, DCM), 0.575 ml of cyclohexyl isocyanide solution (0.2 M, DCM), 0.500 ml of 4-acetamidobenzaldehyde solution (0.3 M, DCM), and 10 µl of perchloric acid (w=20%).

Calculated mass 454.58; found mass 455.4 (ESI-MS)

Example 8

3-(8-benzyloxy-3-butylaminoimidazo[1,2-a]pyridin-2-yl)-phenol (8)

Compound (8) was prepared according to the general synthesis instructions from 1.0 ml of 2-amino-3-benzyloxypyridine solution (0.1 M, DCM), 0.575 ml of n-butyl isocyanide solution (0.2 M, DCM), 0.500 ml of 3-hydroxybenzaldehyde solution (0.3 M, DCM), and 10 µl of perchloric acid (w=20%).

Calculated mass 387.49; found mass 388.4 (ESI-MS)

Example 9

[8-benzyloxy-2-(3,5-dimethoxyphenyl)-imidazo[1,2-a]pyridin-3-ylamino]-acetic acid methyl ester (9)

Compound (9) was prepared according to the general synthesis instructions from 1.0 ml of 2-amino-3-benzyloxypyridine solution (0.1 M, DCM), 0.575 ml of methyl isocyanoacetate solution (0.2 M, DCM), 0.500 ml of 3,5-dimethoxybenzaldehyde solution (0.3 M, DCM), and 10 µl of perchloric acid (w=20%).

Calculated mass 447.50; found mass 448.3 (ESI-MS)

Example 10

[8-benzyloxy-2-(3,5-dimethoxyphenyl)-imidazo[1,2-a]pyridin-3-yl]-cyclohexylamine (10)

Compound (10) was prepared according to the general synthesis instructions from 1.0 ml of 2-amino-3-benzyloxypyridine solution (0.1 M, DCM), 0.575 ml of cyclohexyl isocyanide solution (0.2 M, DCM), 0.500 ml of 3,5-dimethoxybenzaldehyde solution (0.3 M, DCM), and 10 µl of perchloric acid (w=20%).

Calculated mass 457.58; found mass 458.5 (ESI-MS)

Example 11 cyclohexyl-[6,8-dibromo-2-(2-methoxyphenyl)-5-methyl-imidazo[1,2-a]pyridin-3-yl]-amine (11)

Compound (11) was prepared according to the general synthesis instructions from 1.0 ml of 2-amino-3,5-dibromo-6-methylpyridine solution (0.1 M, DCM), 0.575 ml of cyclohexyl isocyanide solution (0.2 M, DCM), 0.500 ml of 2-methoxybenzaldehyde solution (0.3 M, DCM), and 10 µl of perchloric acid (w=20%).

Calculated mass 457.58; found mass 458.5 (ESI-MS)

Example 12

3-[3-(2,6-dimethylphenylamino)-6-nitroimidazo[1,2-a]pyridin-2-yl]-phenol (12)

Compound (12) was prepared according to the general synthesis instructions from 1.0 ml of 2-amino-5-nitropyridine solution (0.1 M, DCM), 0.575 ml of 2,6-dimethylphenyl isocyanide solution (0.2 M, DCM), 0.500 ml of 3-hydroxybenzaldehyde solution (0.3 M, DCM), and 10 µl of perchloric acid (w=20%).

Calculated mass 376.42; found mass 375.3 (ESI-MS)

Example 13

[6-bromo-2-(2-methoxyphenyl)-imidazo[1,2-a]pyridin-3-yl]-(1,1,3,3-tetramethylbutyl)-amine (13)

Compound (13) was prepared according to the general synthesis instructions from 1.0 ml of 2-amino-5-bromopyridine solution (0.1 M, DCM), 0.575 ml of 1,1,3,3-tetramethylbutyl isocyanide solution (0.2 M, DCM), 0.500 ml of 2-methoxybenzaldehyde solution (0.3 M, DCM), and 10 µl of perchloric acid (w=20%).

Calculated mass 430.39; found mass M+H$_2$O=447.3 (ESI-MS)

Example 14

[6,8-dibromo-2-(2,3-dimethoxyphenyl)-5-methylimidazo[1,2-a]pyridin-3-yl]-(1,1,3,3-tetramethylbutyl)-amine (14)

Compound (14) was prepared according to the general synthesis instructions from 1.0 ml of 2-amino-3,5-dibromo-6-methylpyridine solution (0.1 M, DCM), 0.575 ml of 1,1,3,3-tetramethylbutyl isocyanide solution (0.2 M, DCM), 0.500 ml of 2,3-dimethoxybenzaldehyde solution (0.3 M, DCM), and 10 µl of perchloric acid (w=20%).

Calculated mass 553.34; found mass M+H$_2$O=572.1 (ESI-MS)

Example 15 cyclohexyl-(2-phenylimidazo[1,2-a]quinolin-1-yl)-amine (15)

Compound (15) was prepared according to the general synthesis instructions from 1.0 ml of 2-aminoquinoline solution (0.1 M, DCM), 0.575 ml of cyclohexyl isocyanide solution (0.2 M, DCM), 0.500 ml of benzaldehyde solution (0.3 M, DCM), and 10 µl of perchloric acid (w=20%).

Calculated mass 341.46; found mass 342.3 (ESI-MS)

Example 16

[6-(2-cyclohexyl)-5-methylimidazo[1,2-a]pyridin-3-ylamino)-hexyl]-methylidyne ammonium (16)

Compound (16) was prepared according to the general synthesis instructions from 1.0 ml of 2-amino-6- methylpyridine solution (0.1 M, DCM), 0.575 ml of 1,6-diisocyanhexane solution (0.2 M, DCM), 0.500 ml of cyclohexylcarbaldehyde solution (0.3 M, DCM), and 10 µl of perchloric acid (w=20%).

Calculated mass 339.5; found mass 339.4 (ESI-MS)

Example 17

(2,6-dimethylimidazo[1,2-a]pyridin-3-yl)-(1,1,3,3-tetramethylbutyl)-amine (17)

Compound (17) was prepared according to the general synthesis instructions from 1.0 ml of 2-amino-5-methylpyridine solution (0.1 M, DCM), 0.575 ml of 1,1,3,3-tetramethylbutyl isocyanide solution (0.2 M, DCM), 0.500 ml of acetaldehyde solution (0.3 M, DCM), and 10 µl of perchloric acid (w=20%).

Calculated mass 273.4; found mass 274.3 (ESI-MS)

Example 18 cyclohexyl-(2,7-dimethylimidazo[1,2-a]pyridin-3-yl)-amine (18)

Compound (18) was prepared according to the general synthesis instructions from 1.0 ml of 2-amino-4-methylpyridine solution (0.1 M, DCM), 0.575 ml of cyclohexyl isocyanide solution (0.2 M, DCM), 0.500 ml of acetaldehyde solution (0.3 M, DCM), and 10 µl of perchloric acid (w=20%).

Calculated mass 243.4; found mass 244.4 (ESI-MS)

Example 19 cyclohexyl-(2,5,7-trimethylimidazo[1,2-a]pyridin-3-yl)-amine (19)

Compound (19) was prepared according to the general synthesis instructions from 1.0 ml of 2-amino-4,6-dimethylpyridine solution (0.1 M, DCM), 0.575 ml of cyclohexyl isocyanide solution (0.2 M, DCM), 0.500 ml of acetaldehyde solution (0.3 M, DCM) and 10 µl of perchloric acid (w=20%).

Calculated mass 257.4; found mass 258.4 (ESI-MS)

Example 20

[2-(3,4-dimethoxyphenyl)-6-methylimidazo[1,2-a]pyridin-3-yl]-(6-isocyanohexyl)-amine (20)

Compound (20) was prepared according to the general synthesis instructions from 1.0 ml of 2-amino-5-methylpyridine solution (0.1 M, DCM), 0.575 ml of 1,6-diisocyanhexane solution (0.2 M, DCM), 0.500 ml of 3,4-dimethoxybenzaldehyde solution (0.3 M, DCM), and 10 µl of perchloric acid (w=20%).

Calculated mass 394.5; found mass 393.4 (ESI-MS)

Example 21

(2,7-dimethylimidazo[1,2-a]pyridin-3-yl)-(1,1,3,3-tetramethylbutyl)-amine (21)

Compound (21) was prepared according to the general synthesis instructions from 1.0 ml of 2-amino-4-methylpyridine solution (0.1 M, DCM), 0.575 ml of 1,1,3,3-tetramethylbutyl solution (0.2 M, DCM), 0.500 ml of acetaldehyde solution (0.3 M, DCM) and 10 µl of perchloric acid (w=20%).

Calculated mass 273.4; found mass 274.3 (ESI-MS)

Example 22

(2,8-dimethyl-imidazo[1,2-a]pyridin-3-yl)-(1,1,3,3-tetramethylbutyl)-amine (22)

Compound (22) was prepared according to the general synthesis instructions from 1.0 ml of 2-amino-3-methylpyridine solution (0.1 M, DCM), 0.575 ml of 1,1,3,3-tetramethylbutyl solution (0.2 M, DCM), 0.500 ml of acetaldehyde solution (0.3 M, DCM), and 10 µl of perchloric acid (w=20%).

Calculated mass 273.4; found mass 274.4 (ESI-MS)

Example 23

(1,1,3,3-tetramethylbutyl)-(2,5,7-trimethylimidazo[1,2-a]pyridin-3-yl)-amine (23)

Compound (23) was prepared according to the general synthesis instructions from 1.0 ml of 2-amino-4,6-dimethylpyridine solution (0.1 M, DCM), 0.575 ml of 1,1,3,3-tetramethylbutyl solution (0.2 M, DCM), 0.500 ml of acetaldehyde solution (0.3 M, DCM), and 10 µl of perchloric acid (w=20%).

Calculated mass 287.4; found mass 288.4 (ESI-MS)

Example 24

[2-(3,4-dimethoxyphenyl)-7-methylimidazo[1,2-a]pyridin-3-yl]-(6-isocyanohexyl)-amine (24)

Compound (24) was prepared according to the general synthesis instructions from 1.0 ml of 2-amino-4-methylpyridine solution (0.1 M, DCM), 0.575 ml of 1,6-diisocyanhexane solution (0.2 M, DCM), 0.500 ml of 3,4-dimethoxybenzaldehyde solution (0.3 M, DCM), and 10 µl of perchloric acid (w=20%).

Calculated mass 394.5; found mass 393.4 (ESI-MS)

Example 25

(6-isocyanohexyl)-[2-(2-methoxyphenyl)-6-methyl-imidazo[1,2-a]pyridin-3-yl]-amine (25)

Compound (25) was prepared according to the general synthesis instructions from 1.0 ml of 2-amino-5-methylpyridine solution (0.1 M, DCM), 0.575 ml of 1,6-diisocyanhexane solution (0.2 M, DCM), 0.500 ml of 3,4-dimethoxybenzaldehyde solution (0.3 M, DCM), and 10 µl of perchloric acid (w=20%).

Calculated mass 363.5; found mass 363.4 (ESI-MS)

Example 26 cyclohexyl-(2-furan-2-yl-6-trifluoromethylimidazo[1,2-a]pyridin-3-yl)-amine (26)

Compound (26) was prepared according to the general synthesis instructions from 1.0 ml of 2-amirio-4-trifluoromethylpyridine solution (0.1 M, DCM), 0.575 ml of cyclohexyl isocyanide solution (0.2 M, DCM), 0.500 ml of furfural solution (0.3 M, DCM), and 10 µl of perchloric acid (w=20%).

Calculated mass 349.3; found mass 350.3 (ESI-MS)

Example 27

(8-benzyloxy-2-cyclohexylimidazo[1,2-a]pyridin-2-yl)-cyclohexyl-amine (27)

Compound (27) was prepared according to the general synthesis instructions from 1.0 ml of 2-amino-3-benzyloxypyridine solution (0.1 M, DCM), 0.575 ml of cyclohexyl isocyanide solution (0.2 M, DCM), 0.500 ml of cyclohexylcarbaldehyde solution (0.3 M, DCM), and 10 µl of perchloric acid (w=20%).

Calculated mass 403.6; found mass 404.4 (ESI-MS)

Example 28

(8-benzyloxy-2-methyl-imidazo[1,2-a]pyridin-2-yl)-cyclohexyl-amine (28)

Compound (28) was prepared according to the general synthesis instructions from 1.0 ml of 2-amino-3- benzyloxypyridine solution (0.1 M, DCM), 0.575 ml of cyclohexyl isocyanide solution (0.2 M, DCM), 0.500 ml of acetaldehyde solution (0.3 M, DCM), and 10 µl of perchloric acid (w=20%).

Calculated mass 335.4; found mass 336.3 (ESI-MS)

Example 29

(8-benzyloxy-2-methylimidazo[1,2-a]pyridin-3-yl)-(1,1,3,3-tetramethylbutyl)-amine (29)

Compound (29) was prepared according to the general synthesis instructions from 1.0 ml of 2-amino-3-benzyloxypyridine solution (0.1 M, DCM), 0.575 ml of 1,1,3,3-tetramethylbutyl isocyanide solution (0.2 M, DCM), 0.500 ml of acetaldehyde solution (0.3 M, DCM), and 10 µl of perchloric acid (w=20%).

Calculated mass 365.5; found mass 366.5 (ESI-MS)

Example 30

(8-benzyloxy-2-cyclohexylimidazo[1,2-a]pyridin-3-ylamino)-acetic acid methyl ester (30)

Compound (30) was prepared according to the general synthesis instructions from 1.0 ml of 2-amino-3-benzyloxypyridine solution (0.1 M, DCM), 0.575 ml of methyl isocyanoacetate solution (0.2 M, DCM), 0.500 ml of cyclohexylcarbaldehyde solution (0.3 M, DCM), and 10 µl of perchloric acid (w=20%).

Calculated mass 393.5; found mass 394.5 (ESI-MS)

Example 31

(8-benzyloxy-2-methylimidazo[1,2-a]pyridin-3-ylamino)-acetic acid methyl ester (31)

Compound (31) was prepared according to the general synthesis instructions from 1.0 ml of 2-amino-3-benzyloxypyridine solution (0.1 M, DCM), 0.575 ml of methyl isocyanoacetate solution (0.2 M, DCM), 0.500 ml of acetaldehyde solution (0.3 M, DCM), and 10 µl of perchloric acid (w=20%).

Calculated mass 325.4; found mass 326.3 (ESI-MS)

Example 32

Butyl-(2-cyclohexyl-5-propylimidazo[1,2-a]pyridin-3-yl)-amine (32)

Compound (32) was prepared according to the general synthesis instructions from 1.0 ml of 2-amino-6-propylpyridine solution (0.1 M, DCM), 0.575 ml of n-butylisocyanide solution (0.2 M, DCM), 0.500 ml of cyclohexylcarbaldehyde solution (0.3 M, DCM), and 10 µl of perchloric acid (w=20%).

Calculated mass 313.5; found mass 314.5 (ESI-MS)

Example 33

N-cylcohexyl-N-(6,8-dichloro-2-furan-2-yl-imidazo[1,2-a]pyridin-3-yl)-acetamide (33)

Compound (33) was prepared from 1.0 ml of 2-amino-3,5-dichloropyridine solution (0.1 M, DCM), 0.575 ml of cyclohexyl isocyanide solution (0.2 M, DCM), 0.500 ml of furfural solution (0.3 M, DCM), and 10 µl of perchloric acid (w=20%), and reaction with acetyl chloride. Excess acetyl chloride was removed under reduced pressure.

Calculated mass 392.3; found mass 392.3/394.3; M-acetyl 350.4 (ESI-MS)

Example 34

N-cylcohexyl-N-(2-furan-2-yl-6-trifluoromethylimidazo[1,2-a]pyridin-3-yl)-acetamide (34)

Compound (34) was prepared from 1.0 ml of 2-amino-5-trifluoromethylpyridine solution (0.1 M, DCM), 0.575 ml of cyclohexyl isocyanide solution (0.2 M, DCM), 0.500 ml of furfural solution (0.3 M, DCM), and 10 µl of perchloric acid (w=20%), and reaction with acetyl chloride. Excess acetyl chloride was removed under reduced pressure.

Calculated mass 391.4; found mass 392.3; M-acetyl 350.4 (ESI-MS)

Example 35

N-(8-benzyloxy-2-cyclohexylimidazo[1,2-a]pyridin-3-yl)-N-cyclohexyl-acetamide (35)

Compound (35) was prepared from 1.0 ml of 2-amino-3-benzyloxypyridine solution (0.1 M, DCM), 0.575 ml of cyclohexyl isocyanide solution (0.2 M, DCM), 0.500 ml of cyclohexylcarbaldehyde solution (0.3 M, DCM), and 10 µl of perchloric acid (w=20%), and reaction with acetyl chloride. Excess acetyl chloride was removed under reduced pressure.

Calculated mass 445.6; found mass 446.4; M-acetyl 404.4 (ESI-MS)

Example 36

(5-methyl-2-phenanthren-9-yl-imidazo[1,2-a]pyridin-3-yl)-(1,1,3,3-tetramethylbutyl)-amine (36)

Compound (36) was prepared according to the general synthesis instructions from 1.0 ml of 2-amino-6-methylpyridine solution (0.1 M, DCM), 0.575 ml of 1,1,3,3-tetramethylbutyl isocyanide solution (0.2 M, DCM), 0.500 ml of phenanthrene-9-carbaldehyde solution (0.3 M, DCM), and 10 µl of perchloric acid (w=20%).

Calculated mass 435.6; found mass 436.5 (ESI-MS)

Example 37

(2-anthracen-9-yl-7-methylimidazo[1,2-a]pyrimidin-3-yl)-(1,1,3,3-tetramethylbutyl)-amine (37)

Compound (37) was prepared according to the general synthesis instructions from 1.0 ml of 2-amino-4-methylpyrimidine solution (0.1 M, DCM), 0.575 ml of 1,1,3,3-tetramethylbutyl isocyanide solution (0.2 M, DCM), 0.500 ml of anthracene-9-carbaldehyde solution (0.3 M, DCM), and 10 µl of perchloric acid (w=20%).

Calculated mass 436.6; found mass 437.3 (ESI-MS)

Example 38 cyclohexyl-[7-methyl-2-(1-methyl-1H-pyrrol-2-yl)-imidazo[1,2-a]pyrimidin-3-yl]-amine (38)

Compound (38) was prepared according to the general synthesis instructions from 1.0 ml of 2-amino-4-methylpyrimidine solution (0.1 M, DCM), 0.575 ml of cyclohexyl isocyanide solution (0.2 M, DCM), 0.500 ml of N-methylpyrrole-2-carbaldehyde solution (0.3 M, DCM), and 10 µl of perchloric acid (w=20%).

Calculated mass 309.4; found mass 310.4 (ESI-MS)

The compounds according to the invention prove to be effective as ligands for the pain-relevant α2-subtype of the human α-adrenergic receptor. The affinity for the α2-subtype of the human α-adrenergic receptor was determined by means of a SPA assay conventionally used for high throughput screening as described in John P. Devlin, *High Throughput Screening*, Marcel Dekker Inc. 1997, pp. 307 to 316. This literature is introduced here as a reference and thus forms part of the disclosure. At a concentration of 10 μM, the following affinities for the listed examples were determined:

|  | α2-affinity, 10 μM |
|---|---|
| Example 16 | 67% |
| Example 17 | 65% |
| Example 18 | 74% |
| Example 19 | 81% |
| Example 20 | 85% |
| Example 21 | 109% |
| Example 22 | 69% |
| Example 23 | 97% |
| Example 24 | 75% |
| Example 25 | 51% |
| Example 26 | 70% |
| Example 27 | 77% |
| Example 28 | 80% |
| Example 29 | 100% |
| Example 30 | 60% |
| Example 31 | 61% |
| Example 32 | 61% |
| Example 33 | 73% |
| Example 34 | 72% |
| Example 35 | 75% |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

We claim:

1. A compound of formula I,

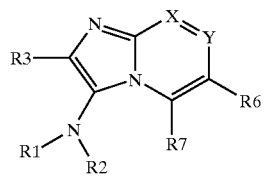

wherein
X denotes $CR^4$, and Y denotes $CR^5$;
$R^1$ denotes
  $(CH_2)_n CN$ where n=4, 5, or 6,
  optionally substituted phenyl,
  $C_4-C_8$-cycloalkyl,
  $CH_2CH_2R$ wherein R=morpholino,
  1,1,3,3-tetramethylbutyl, or
  $CH_2R^a$
    wherein $R^a$ denotes hydrogen, OH, branched or unbranched $C_1-C_8$-alkyl, optionally substituted phenyl, CO(OR') wherein R'=unbranched $C_1-C_4$-alkyl or branched $C_1-C_5$-alkyl, $PO(OR')_2$ wherein R'=unbranched $C_1-C_4$-alkyl or branched $C_1-C_5$-alkyl, or $Si(R^xR^yR^z)$ wherein $R^x$, $R^y$ and $R^z$ are each independently selected from the group consisting of branched or unbranched $C_1-C_4$-alkyl, $C_4-C_8$-cycloalkyl, and phenyl;

$R^2$ denotes
  hydrogen,
  $COR^b$ wherein $R^b$ denotes branched or unbranched $C_1-C_4$-alkyl, or $C_3-C_8$-cycloalkyl,
  $CH_2CH_2CO(OR^c)$ wherein $R^c$ denotes branched or unbranched $C_1-C_4$-alkyl, adamantyl, optionally substituted phenyl, optionally substituted 1-naphthyl, optionally substituted 2-naphthyl, optionally substituted 2-pyridyl, optionally substituted 3-pyridyl, optionally substituted 4-pyridyl, optionally substituted thiazolyl, or optionally substituted furoyl,
  benzyl,
  $CH_2CH_2R^d$ wherein $R^d$ denotes optionally substituted phenyl, or
  $CONHR^e$, wherein $R^e$ is selected from the group consisting of branched or unbranched $C_1-C_8$-alkyl, $C_3-C_8$-cycloalkyl, and optionally substituted phenyl;

$R^3$ denotes
  branched or unbranched $C_1-C_8$-alkyl,
  $C_3-C_8$-cycloalkyl,
  optionally substituted phenyl,
  optionally substituted naphthyl,
  optionally substituted pyrrole,
  optionally substituted pyridyl,
  optionally substituted furan,
  optionally substituted thiophene,
  optionally substituted anthracene,
  optionally substituted phenanthrene or
  optionally substituted quinoline, $R^4$, $R^5$, $R^6$ and $R^7$ are each independently selected from the group consisting of hydrogen, $NO_2$, $NH_2$, OH, $CF_3$, Cl, F, Br, CN, methyl, and OR" wherein R"=benzyl; or $R^6$ and $R^7$ together form a bridge —CH=CH—CH=CH— and the radicals $R^4$ and $R^5$, if present, denote hydrogen;

wherein any radical denoted optionally substituted is unsubstituted, or is at least mono-substituted with a moiety selected from the group consisting of OH, nitro, amino, amido, cyano, CO—$C_1-C_8$-alkyl, CO—O—$C_1-C_8$-alkyl, $CO_2H$, O—$C_1-C_8$-alkyl, O-heteroalkyl, halogen, branched or unbranched $C_1-C_8$-alkyl, $C_3-C_8$-cycloalkyl, $C_3-C_8$-heterocyclyl, unsubstituted or substituted phenyl, unsubstituted or substituted heteroaryl, wherein any ring, aromatic or unsaturated, may be fused to other rings, any moiety optionally has one or more double or triple bonds, and any alkyl or aromatic moiety is unsubstituted or is substituted with a moiety selected from this group;

with the proviso that at least one of the radicals $R^4$, $R^5$, $R^6$, or $R^7$ present in the molecule is not hydrogen;

with the further proviso that if $R^1$ is methyl, ethyl, propyl, n-butyl, isobutyl, CO(O-methyl) or benzyl, $R^3$ is not methyl;

with the further proviso that if one of the radicals $R^4$, $R^5$, $R^6$, and $R^7$;

is OR" wherein R" denotes benzyl, $R^1$ is not $CH_2R^a$, wherein $R^a$ denotes hydrogen or branched or unbranched $C_1-C_5$ alkyl;

or a pharmaceutically acceptable salt thereof.

2. A compound according to claim 1, wherein
$R^2$ denotes hydrogen;
$R^1$ is selected from the group consisting of $(CH_2)_n CN$ where n=4, 5 or 6, cyclohexyl, $CH_2CO(O$-methyl$)$, 2,6-dimethylphenyl, 1,1,3,3-tetramethylbutyl, and n-butyl; and

17

$R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)-phenyl.

3. A compound according to claim 1, selected from the group consisting of

[6-bromo-2-(2-methoxyphenyl)-imidazo[1,2-a]pyridin-3-yl]-1,1,3,3-tetramethyyl]butyl)-amine,
N-[4-(8-benzyloxy-3-cyclohexylaminoimidazo[1,2-a]pyridin-2-yl)-phenyl]-acetamide,
3-(8-benzyloxy-3-butylaminoimidazo[1,2-a]pyridin-2-yl)-phenol,
[8-benzyloxy-2-(3,5-dimethoxyphenyl)-imidazo[1,2-a]pyridin-3-ylamino]-acetic acid methyl ester,
[8-benzyloxy-2-(3,5-dimethoxyphenyl)-imidazo[1,2-a]pyridin-3-yl]-cyclohexylamine,
cyclohexyl-[6,8-dibromo-2-(2-methoxyphenyl)-5-methyl-imidazo[1,2-a]pyridin-3-yl]-amine,
3-[3-(2,6-dimethylphenylamino)-6-nitroimidazo[1,2-a]pyridin-2-yl]-phenol,
[6-bromo-2-(2-methoxyphenyl)-imidazo[1,2-a]pyridin-3-yl]-(1,1,3,3-tetramethylbutyl)-amine,
[6,8-dibromo-2-(2,3-dimethoxyphenyl)-5-methylimidazo[1,2-a]pyridin-3-yl]-(1, 1,3,3-tetramethylbutyl)-amine,
cyclohexyl-(2-phenylimidazo[1,2-a]quinolin-1-yl)-amine,
[6-(2-cyclohexyl]-5-methylimidazo[1,2-a]pyridin-3-ylamino)-hexyl]-methylidyne ammonium,
(2,6-dimethylimidazo[1,2-a]pyridin-3-yl)-(1,1,3,3-tetramethylbutyl)-amine,
cyclohexyl-(2,7-dimethylimidazo[1,2-a]pyridin-3-yl)-amine,
cyclohexyl-(2,5,7-trimethylimidazo[1,2-a]pyridin-3-yl)-amine,
[2-(3,4-dimethoxyphenyl)-6-methylimidazo[1,2-a]pyridin-3-yl]-(6-isocyanohexyl)-amine,
(2,7-dimethylimidazo[1,2-a]pyridin-3-yl)-(1,1,3,3-tetramethylbutyl)-amine,
(2,8-dimethyl-imidazo[1,2-a]pyridin-3-yl)-(1,1,3,3-tetramethylbutyl)-amine,
(1,1,3,3-tetramethylbutyl)-(2,5,7-trimethylimidazo[1,2-a]pyridin-3-yl)-amine,
[2-(3,4-dimethoxyphenyl)-7-methylimidazo[1,2-a]pyridin-3-yl]-(6-isocyanohexyl)-amine,
(6-isocyanohexyl)-[2-(2-methoxyphenyl)-6-methyl-imidazo[1,2-a]pyridin-3-yl]-amine,
cyclohexyl-(2-furan-2-yl-6-trifluoromethyl-imidazo[1,2-a]pyridin-3-yl)-amine,
(8-benzyloxy-2-cyclohexylimidazo[1,2-a]pyridin-3-yl)-cyclohexylamine,
(8-benzyloxy-2-methyl-imidazo[1,2-a]pyridin-3-yl)-cyclohexylamine,
(8-benzyloxy-2-methylimidazo[1,2-a]pyridin-3-yl)-(1,1,3,3-tetramethylbutyl)-amine,
(8-benzyloxy-2-cyclohexylimidazo[1,2-a]pyridin-3-ylamino)-acetic acid methyl ester,
(8-benzyloxy-2-methylimidazo[1,2-a]pyridin-3-ylamino)-acetic acid methyl ester,
butyl-(2-cyclohexyl-5-propylimidazo[1,2-a]pyridin-3-yl)-amine,

18

N-cylcohexyl-N-(6,8-dichloro-2-furan-2-yl-imidazo[1,2-a]pyridin-3-yl)-acetamide,
N-cylcohexyl-N-(2-furan-2-yl-6-trifluoromethyl-imidazo[1,2-a]pyridin-3-yl)-acetamide,
N-(8-benzyloxy-2-cyclohexylimidazo[1,2-a]pyridin-3-yl)-N-cyclohexyl-acetamide, and
(5-methyl-2-phenanthren-9-yl-imidazo[1,2-a]pyridin-3-yl)-(1,1,3,3-tetramethylbutyl)-amine.

4. A process for preparing at least one compound according to claim 1, comprising
  selecting amidine, aldehyde, and isonitrile as starting materials;
  solvating said starting materials in at least one halogenated alkane as a solvent;
  adding said starting materials to a reaction vessel successively in sequence (a) amidine, (b) aldehyde, and (c) isonitrile;
  forming a three-component reaction thereby;
  adding perchloric acid to at least one of said starting materials or reaction vessel; and
  preparing at least one compound according to claim 1 thereby.

5. A process according to claim 4, further comprising reacting products formed in said three component reaction with R2Hal or with ReNCO, wherein Hal denotes bromine, iodine, or chlorine.

6. The process according to claim 5, wherein Hal denotes chlorine.

7. A pharmaceutical composition comprising at least one compound according to claim 1 and at least one auxiliary substance selected from the group consisting of carrier materials, fillers, solvents, diluents, coloring agents and binders.

8. A pharmaceutical composition according to claim 7, wherein in said at least one compound
  $R^2$ denotes hydrogen;
  $R^1$ is selected from the group consisting of $(CH_2)_nCN$ where n=4,5 or 6, cyclohexyl, $CH_2CO(O$-methyl), 2,6-dimethylphenyl, 1,1,3,3-tetramethylbutyl, and n-butyl; and
  $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)-phenyl.

9. A pharmaceutical composition according to claim 7, wherein said at least one compound is selected from the group consisting of

[6-bromo-2-(2-methoxyphenyl)-imidazo[1,2-a]pyridin-3-yl]-1,1,3,3-tetramethyyl butyl)-amine,
N-[4-(8-benzyloxy-3-cyclohexylaminoimidazo[1,2-a]pyridin-2-yl)phenyl]-acetamide,
3-(8-benzyloxy-3-butylaminoimidazo[1,2-a]pyridin-2-yl)-phenol,
[8-benzyloxy-2-(3,5-dimethoxyphenyl)-imidazo[1,2-a]pyridin-3-ylamino]-acetic acid methyl ester,
[8-benzyloxy-2-(3,5-dimethoxyphenyl)-imidazo[1,2-a]pyridin-3-yl]-cyclohexylamine,
cyclohexyl-[6,8-dibromo-2-(2-methoxyphenyl)5-methyl-imidazo[1,2-a]pyridin-3-yl]-amine, 3-[3-(2,6-dimethylphenylamino)-6-nitroimidazo[1,2-a]pyridin-2-yl]-phenol,
[6-bromo-2-(2-methoxyphenyl)-imidazo[1,2-a]pyridin-3-yl]-(1,1,3,3-tetramethylbutyl)-amine,
[6,8-dibromo-2-(2,3-dimethoxyphenyl)-5-methylimidazo-[1,2-a]pyridin-3-yl]-(1,1,3,3-tetramethylbutyl)-amine,
cyclohexyl-(2-phenylimidazo[1,2-a]quinolin-1-yl)-amine,
[6-(2-cyclohexyl]-5-methylimidazo[1,2-a]pyridin-3-ylamino)-hexyl]-methylidyne ammonium,
(2,6-dimethylimidazo[1,2-a]pyridin-3-yl)-(1,1,3,3-tetramethylbutyl)-amine,
cyclohexyl-(2,7-dimethylimidazo[1,2-a]pyridin-3-yl)-amine,
cyclohexyl-(2,5,7-trimethylimidazo[1,2-a]pyridin-3-yl)amine,
[2-(3,4-dimethoxyphenyl)-6-methylimidazo[1,2-a]pyridin-3-yl]-(6-isocyanohexyl)-amine,
(2,7-dimethylimidazo[1,2-a]pyridin-3-yl)-(1,1,3,3-tetramethylbutyl)-amine,
(2,8-dimethyl-imidazo[1,2-a]pyridin-3-yl)-(1,1,3,3-tetramethylbutyl)-amine,
(1,1,3,3-tetramethylbutyl)-(2,5,7-trimethylimidazo-[1,2-a]pyridin-3-yl)-amine,
[2-(3,4-dimethoxyphenyl)-7-methylimidazo[1,2-a]pyridin-3-yl]-(6-isocyanohexyl)-amine, and
(6-isocyanohexyl)-[2-(2-methoxyphenyl)-6-methyl-imidazo[1,2-a]pyridin-3-yl]-amine,
cyclohexyl-(2-furan-2-yl-6-trifluoromethylimidazo-[1,2-a]pyridin-3-yl)-amine,
(8-benzyloxy-2-cyclohexylimidazo[1,2-a]pyridin-3-yl)-cyclohexyl-amine,
(8-benzyloxy-2-methyl-imidazo[1,2-a]pyridin-3-yl)-cyclohexyl-amine,
(8-benzyloxy-2-methylimidazo[1,2-a]pyridin-3-yl)-(1,1,3,3-tetramethylbutyl)-amine,
(8-benzyloxy-2-cyclohexylimidazo[1,2-a]pyridin-3-ylamino)-acetic acid methyl ester,
(8-benzyloxy-2-methylimidazo[1,2-a]pyridin-3-ylamino)-acetic acid methyl ester,
butyl-(2-cyclohexyl-5-propylimidazo[1,2-a]pyridin-3-yl) amine,
N-cylcohexyl-N-(6,8-dichloro-2-furan-2-yl-imidazo[1,2-a]pyridin-3-yl)-acetamide,
N-cylcohexyl-N-(2-furan-2-yl-6-trifluoromethyl-imidazo[1,2-a]pyridin-3-yl)-acetamide,
N-(8-benzyloxy-2-cyclohexylimidazo[1,2-a]pyridin-3-yl)-N-cyclohexyl-acetamide, and
(5-methyl-2-phenanthren-9-yl-imidazo[1,2-a]pyridin-3-yl)-(1,1,3,3-tetramethylbutyl)-amine.

10. A method of alleviating pain, comprising administering to a patient in need thereof a pain alleviating amount of at least one compound of formula I,

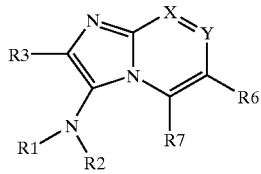

I wherein
X denotes $CR^4$, and Y denotes $CR^5$;
$R^1$ denotes $(CH_2)_nCN$ where n=4, 5, or 6, optionally substituted phenyl, $C_4$–$C_8$-cycloalkyl, $CH_2$, $CH_2R$ wherein R=4-morpholino, 1,1,3,3-tetramethylbutyl, $CH_2R^a$ wherein $R^a$ denotes hydrogen, OH, branched or unbranched $C_1$–$C_8$-alkyl, optionally substituted phenyl, CO(OR') wherein R'=unbranched $C_1$–$C_4$-alkyl or branched $C_1$–$C_5$-alkyl, $PO(OR')_2$ wherein R'=unbranched $C_1$–$C_4$-alkyl or branched $C_1$–$C_5$-alkyl, or $Si(R^xR^yR^z)$ wherein $R^x$, $R^y$ and $R^z$ are each independently selected from the group consisting of branched or unbranched $C_1$–$C_4$-alkyl, $C_4$–$C_8$-cycloalkyl, and phenyl;
$R^2$ denotes hydrogen, $COR^b$ wherein $R^b$ denotes branched or unbranched $C_1$–$C_4$-alkyl, or $C_3$–$C_8$-cycloalkyl, $CH_2CH_2CO(OR^c)$ wherein $R^c$ denotes branched or unbranched $C_1$–$C_4$-alkyl, adamantyl, optionally substituted phenyl, optionally substituted 1-naphthyl, optionally substituted 2-naphthyl, optionally substituted 2-pyridyl, optionally substituted 3-pyridyl, optionally substituted 4-pyridyl, optionally substituted thiazolyl, optionally substituted furoyl, $CH_2$-phenyl, $CH_2CH_2R^d$ wherein $R^d$ denotes optionally substituted phenyl, or $CONHR^e$, wherein $R^e$ denotes branched or unbranched $C_1$–$C_8$-alkyl, $C_3$–$C_8$-cycloalkyl, or optionally substituted phenyl;
$R^3$ denotes branched or unbranched $C_1$–$C_8$-alkyl,
$C_3$–$C_8$-cycloalkyl,
optionally substituted phenyl,
optionally substituted naphthyl,
optionally substituted pyrrole,
optionally substituted pyridyl,
optionally substituted furan,
optionally substituted thiophene,
optionally substituted anthracene,
optionally substituted phenanthrene or
optionally substituted quinoline;
$R^4$, $R^5$, $R^6$ and $R^7$ are each independently selected from the group consisting of hydrogen, $NO_2$, $NH_2$, OH, $CF_3$, Cl, F, Br, CN, methyl, and OR" wherein R"=benzyl; or
$R^6$ and $R^7$ together form a bridge —CH=CH—CH=CH— and the radicals $R^4$ and $R^5$, if present, denote hydrogen;
wherein any radical denoted optionally substituted is unsubstituted, or is at least mono-substituted with a moiety selected from the group consisting of OH, nitro, amino, amido, cyano, CO—C1–C8-alkyl, CO—O—C1–C8-alkyl, CO2H, O—C1–C8-alkyl, O-heteroalkyl, halogen, branched or unbranched C1–C8-alkyl, C3–C8-cycloalkyl, C3–C8-heterocyclyl, unsubstituted or substituted phenyl, unsubstituted or substituted heteroaryl, wherein any ring, aromatic or unsaturated, may be fused to other rings, any moiety optionally has one or more double or triple bonds, and any alkyl or aromatic moiety is unsubstituted or is substituted with a moiety selected from this group;
with the proviso that at least one of the radicals $R^4$, $R^5$, $R^6$, or $R^7$ present in the molecule is not hydrogen;
with the further proviso that if $R^1$ is methyl, ethyl, propyl, n-butyl, isobutyl, CO(O-methyl) or benzyl, $R^3$ is not methyl;
with the further proviso that if $R^a$ is hydrogen or branched or unbranched $C_1$–$C_5$ alkyl, and one of the radicals $R^4$, $R^5$, $R^6$, and $R^7$ is O-benzyl, $R^1$ is not $CH_2R^a$;

with the further proviso that if $R^4$ is OR" wherein R" denotes benzyl, $R^1$ is not $CH_2R^a$, wherein $R^a$ denotes hydrogen or branched or unbranched $C_1$–$C_5$ alkyl;
or a pharmaceutically acceptable salt thereof.

11. A method according to claim 10, wherein said compound is administered in combination with at least one auxiliary substance selected from the group consisting of carrier materials, fillers, solvents, diluents, coloring agents and binders.

12. A method according to claim 10, wherein $R^2$ denotes hydrogen;

$R^1$ is selected from the group consisting of $(CH_2)_nCN$ where n=4, 5 or 6, cyclohexyl, $CH_2CO(O\text{-methyl})$, 2,6-dimethylphenyl, 1,1,3,3-tetramethylbutyl, and n-butyl; and $R^3$ is selected from the group consisting of 2-pyridyl, 3-pyridyl, 2-furanyl, 2-pyrroyl, methyl, tert-butyl, 3-hydroxyphenyl, 3,4-dimethoxyphenyl, 2,3-dichlorophenyl, 2,4-dichlorophenyl, 2-methoxyphenyl, 2,3-dimethoxyphenyl, 3-bromophenyl, 4-bromo-2-fluorophenyl, 5-bromo-2-fluorophenyl, 3-bromo-4-fluorophenyl, 3-chlorophenyl, 3,4-dichlorophenyl, 3-fluorophenyl, 3-methylphenyl, 3-phenoxyphenyl, 3-(4-chlorophenoxy)phenyl, 2-chloro-4-fluorophenyl, 2-chloro-6-fluorophenyl, 2,4-dimethylphenyl, 2,5-dimethylphenyl, 2-bromophenyl, 2-fluorophenyl, and 2-(trifluoromethyl)-phenyl.

13. A method according to claim 10, wherein said at least one compound is selected from the group consisting of

[6-bromo-2-(2-methoxyphenyl)-imidazo[1,2-a]pyridin-3-yl]-1,1,3,3-tetramethyyl]butyl)-amine,
N-[4-(8-benzyloxy-3-cyclohexylaminoimidazo[1,2-a]pyridin-2-yl)phenyl]-acetamide,
3-(8-benzyloxy-3-butylaminoimidazo[1,2-a]pyridin-2-yl)-phenol,
[8-benzyloxy-2-(3,5-dimethoxyphenyl)-imidazo[1,2-a]pyridin-3-ylamino]-acetic acid methyl ester,
[8-benzyloxy-2-(3,5-dimethoxyphenyl)-imidazo[1,2-a]pyridin-3-yl]-cyclohexylamine,
cyclohexyl-[6,8-dibromo-2-(2-methoxyphenyl)-5-methyl-imidazo[1,2-a]pyridin-3-yl]-amine,
3-[3-(2,6-dimethylphenylamino)-6-nitroimidazo[1,2-a]pyridin-2-yl]-phenol,
[6-bromo-2-(2-methoxyphenyl)-imidazo[1,2-a]pyridin-3-yl]-(1,1,3,3-tetramethylbutyl)-amine,
[6,8-dibromo-2-(2,3-dimethoxyphenyl)-5-methylimidazo[1,2-a]pyridin-3-yl]-(1,1,3,3-tetrarnethylbutyl)-amine,
cyclohexyl-(2-phenylimidazo[1,2-a]quinolin-1-yl)-amine,
[6-(2-cyclohexyl]-5-methylimidazo[1,2-a]pyridin-3-ylamino)-hexyl]-methylidyne ammonium,
(2,6-dimethylimidazo[1,2-a]pyridin-3-yl)-(1,1,3,3-tetramethylbutyl)-amine,
cyclohexyl-(2,7-dimethylimidazo[1,2-a]pyridin-3-yl)-amine,
cyclohexyl-(2,5,7-trimethylimidazo[1,2-a]pyridin-3-yl)-amine,
[2-(3,4-dimethoxyphenyl)-6-methylimidazo[1,2-a]pyridin-3-yl]-(6-isocyanohexyl)-amine,
(2,7-dimethylimidazo[1,2-a]pyridin-3-yl)-(1,1,3,3-tetramethylbutyl)-amine,
(2,8-dimethyl-imidazo[1,2-a]pyridin-3-yl)-(1,1,3,3-tetranethylbutyl)-amine,
(1,1,3,3-tetramethylbutyl)-(2,5,7-trimethylimidazo[1,2-a]pyridin-3-yl)-amine,
[2-(3,4-dimethoxyphenyl)-7-methylimidazo[1,2-a]pyridin-3-yl]-(6-isocyanohexyl)-amine,
(6-isocyanohexyl)-[2-(2-methoxyphenyl)-6-methyl-imidazo[1,2-a]pyridin-3-yl]-amine,
cyclohexyl-(2-furan-2-yl-6-trifluoromethyl-imidazo[1,2-a]pyridin-3-yl)-amine,
(8-benzyloxy-2-cyclohexylimidazo[1,2-a]pyridin-3-yl)-cyclohexylamine,
(8-benzyloxy-2-methyl-imidazo[1,2-a]pyridin-3-yl)-cyclohexylamine,
(8-benzyloxy-2-methylimidazo[1,2-a]pyridin-3-yl)-(1,1,3,3-tetramethylbutyl)-amine,
(8-benzyloxy-2-cyclohexylimidazo[1,2-a]pyridin-3-ylamino)-acetic acid methyl ester,
(8-benzyloxy-2-methylimidazo[1,2-a]pyridin-3-ylamino)-acetic acid methyl ester,
butyl-(2-cyclohexyl-5-propylimidazo[1,2-a]pyridin-3-yl)-amine,
N-cylcohexyl-N-(6,8-dichloro-2-furan-2-yl-imidazo[1,2-a]pyridin-3-yl)acetamide,
N-cylcohexyl-N-(2-furan-2-yl-6-trifluoromethyl-imidazo[1,2-a]pyridin-3-yl)-acetamide,
N-(8-benzyloxy-2-cyclohexylimidazo[1,2-a]pyridin-3-yl)-N-cyclohexyl-acetamide, and
(5-methyl-2-phenanthren-9-yl-imidazo[1,2-a]pyridin-3-yl)-(1,1,3,3-tetramethylbutyl)-amine.

* * * * *